(12) United States Patent
Hickingbotham

(10) Patent No.: US 7,837,372 B2
(45) Date of Patent: Nov. 23, 2010

(54) VARIABLE INTENSITY ENDOILLUMINATOR

(75) Inventor: Dyson Hickingbotham, Wake Forest, NC (US)

(73) Assignee: Alcon, Inc., Hunenberg (CH)

( * ) Notice: Subject to any disclaimer, the term of this patent is extended or adjusted under 35 U.S.C. 154(b) by 290 days.

(21) Appl. No.: 12/144,410

(22) Filed: Jun. 23, 2008

(65) Prior Publication Data

US 2009/0030406 A1   Jan. 29, 2009

Related U.S. Application Data

(60) Provisional application No. 60/945,392, filed on Jun. 21, 2007.

(51) Int. Cl.
*F21S 4/00* (2006.01)
(52) U.S. Cl. ........................ 362/572; 362/552; 362/558; 362/551
(58) Field of Classification Search .................. 362/572, 362/574, 575, 577, 582, 551, 552, 553, 558; 606/4, 15
See application file for complete search history.

(56) References Cited

U.S. PATENT DOCUMENTS

| 4,772,093 | A | 9/1988 | Abele et al. |
| 4,919,130 | A * | 4/1990 | Stoy et al. .................. 606/107 |
| 5,058,985 | A | 10/1991 | Davenport et al. |
| 5,725,514 | A | 3/1998 | Grinblat et al. |
| 5,784,508 | A | 7/1998 | Turner |
| 6,458,120 | B1 | 10/2002 | Shen et al. |
| 2005/0075628 | A1 * | 4/2005 | Cazzini et al. ................. 606/4 |
| 2007/0100327 | A1 | 5/2007 | Smith |

* cited by examiner

*Primary Examiner*—Ali Alavi
(74) *Attorney, Agent, or Firm*—Armando Pastrana, Jr.

(57) ABSTRACT

A variable intensity endoilluminator system is disclosed, one embodiment comprising: a light source for providing a light beam; an optical cable, optically coupled to the light source for receiving and transmitting the light beam; a handpiece, operably coupled to the optical cable to receive the light beam; an optical fiber, operably coupled to the handpiece, wherein the optical fiber is optically coupled to the optical cable to receive and transmit the light beam to illuminate a surgical field; and a translucent cannula, operably coupled to the handpiece, for housing and directing the optical fiber, wherein the cannula is operable to diffuse and transmit the light from the light beam when the optical fiber is retracted into the cannula. The cannula and the handpiece can be fabricated from biocompatible materials.

10 Claims, 3 Drawing Sheets

VARIABLE INTENSITY ENDOILLUMINATOR

This application claims priority from the provisional application, U.S. Patent Application Ser. No. 60/945,392 filed Jun. 21, 2007.

TECHNICAL FIELD OF THE INVENTION

The present invention relates generally to surgical instrumentation. In particular, the present invention relates to surgical instruments for illuminating an area during eye surgery. Even more particularly, the present invention relates to a variable intensity endoilluminator having a moveable optical fiber to provide spot or diffused illumination of a surgical site.

BACKGROUND OF THE INVENTION

In ophthalmic surgery, and in particular in vitreo-retinal surgery, it is desirable to use a wide-angle surgical microscope system to view as large a portion of the retina as possible. Wide-angle objective lenses for such microscopic systems exist, but they require a wider illumination field than that provided by the cone of illumination of a typical fiber-optic probe. As a result, various technologies have been developed to increase the beam spreading of the relatively incoherent light provided by a fiber-optic illuminator. These known wide-angle endoilluminators can thus illuminate a larger portion of the retina as required by current wide-angle surgical microscope systems.

While it is generally desirable to illuminate (view) as large a portion of an ophthalmic surgical field as possible, it is also desirable at certain points during a surgical procedure to provide a more precise spotlight to show fine details. Prior art solutions exist to provide both general illumination of a surgical field and its peripheral areas and spot illumination of a smaller area. These prior art solutions, however, suffer from the disadvantage of needing more than one instrument to provide such dual lighting capability.

For example, prior art solutions include providing illumination to peripheral areas of a surgical field via one entry site into the eye, while providing spot illumination with a standard fiber optic probe inserted via a different entry site. Another solution for providing peripheral lighting has been to insert a chandelier probe via, potentially, yet another entry site into the eye. Proper lighting of a surgical field has thus typically required multiple incisions to provide entry points into the eye for multiple illuminators. It is generally desirable to limit the number incisions on an eye during surgery.

Separate peripheral (general) lighting of a surgical field is required because a standard fiber optic probe, typically housed in a metal cannula, cannot provide such peripheral lighting, and a wide-angle illuminator, while capable of providing a broader range of illumination, cannot provide a precise spotlight to illuminate finer details of a surgical site, as can a standard fiber optic illuminator. Thus, no single prior art endoilluminator has been developed that can provide, alternatively, diffuse light to provide general illumination of a surgical field and peripheral areas and a precise spotlight to illuminate a smaller area to show greater detail.

Therefore, a need exists for a surgical variable intensity endoilluminator that can reduce or eliminate these and other problems associated with prior art illuminators.

BRIEF SUMMARY OF THE INVENTION

The embodiments of a variable intensity endoilluminator of the present invention substantially meet these needs and others. One embodiment of the present invention is a small-gauge, variable intensity wide-angle illumination surgical system comprising: a light source for providing a light beam; an optical cable, optically coupled to the light source for receiving and transmitting the light beam; a handpiece, operably coupled to the optical cable to receive the light beam; an optical fiber, operably coupled to the handpiece, wherein the optical fiber is optically coupled to the optical cable to receive and transmit the light beam to illuminate a surgical field; and a translucent cannula, operably coupled to the handpiece, for housing and directing the optical fiber, wherein the cannula is operable to diffuse and transmit the light from the light beam when the optical fiber is retracted into the cannula.

The optical fiber can be a small-gauge optical fiber the distal end of which, in an extended position, is co-incident with the distal end of the cannula. For example, the optical fiber can be sized for housing within a 19, 20, 23 or 25 gauge cannula (e.g., about 0.75 mm to about 0.4 mm diameter optical fiber). Further, the cannula, optical fiber and the handpiece can be fabricated from biocompatible materials. The optical cable can comprise a first optical connector operably coupled to the light source and a second optical connector operably coupled to the handpiece (to optically couple the optical cable to the optical fiber housed within the handpiece and cannula). These connectors can be SMA optical fiber connectors. The optical fiber and optical cable (i.e., the optical fiber(s) within the optical cable) are of compatible gauge so as to transmit the light beam from the light source to the surgical field. For example, they can be of equal gauge.

In the embodiments of this invention, the optical fiber can be operably coupled to the handpiece to enable linear displacement of the optical fiber within the cannula. The handpiece can include means, such as a lever, a push/pull mechanism, or other mechanical, magnetic or electric displacement device, as will be known to those having skill in the art, for adjusting the linear displacement of the optical fiber. Other adjusting means as known to those in the art can also be used. Adjusting the linear displacement of the optical fiber will change the position of the optical fiber between a fully extended position (distal end of optical fiber coincident with the distal end of the cannula) and a retracted position at which the optical fiber's distal end is positioned inside the cannula upstream of the cannula's distal end. By adjusting the linear displacement of the optical fiber, a surgeon can adjust the illuminator such that it will provide spot illumination or more diffuse light to illuminate peripheral areas of the surgical field (e.g., the retina of an eye).

Other embodiments of the present invention can include a method for variable intensity illumination of a surgical field using an endoilluminator having a moveable fiber to provide spot or diffused illumination of a surgical site in accordance with the teachings of this invention, and a surgical handpiece embodiment of the variable intensity endoilluminator of the present invention for use in ophthalmic surgery. Further, embodiments of this invention can be incorporated within a surgical machine or system for use in ophthalmic or other surgery. Other uses for a variable intensity endoilluminator designed in accordance with the teachings of this invention will be known to those having skill in the art.

BRIEF DESCRIPTION OF THE SEVERAL VIEWS OF THE DRAWINGS

A more complete understanding of the present invention and the advantages thereof may be acquired by referring to the following description, taken in conjunction with the accompanying drawings, in which like reference numbers indicate like features and wherein.

DETAILED DESCRIPTION OF THE INVENTION

Preferred embodiments of the present invention are illustrated in the FIGURES, like numerals being used to refer to like and corresponding parts of the various drawings.

The various embodiments of the present invention provide for a small gauge (e.g., 19, 20, 23 or 25 gauge) optical fiber based endo-illuminator device for use in surgical procedures, such as in vitreo-retinal/posterior segment surgery. Embodiments of this invention can comprise a handpiece, such as the Alcon-Grieshaber Revolution-DSP™ handpiece sold by Alcon Laboratories, Inc., of Fort Worth, Tex., connected to a small gauge cannula (e.g., 19, 20, 23 or 25 gauge). The inner dimension of the cannula can be used to house one, or a plurality of, optical fibers in accordance with the teachings of this invention. Embodiments of the variable intensity illuminator can be configured for use in the general field of ophthalmic surgery. However, it is contemplated and it will be realized by those skilled in the art that the scope of the present invention is not limited to ophthalmology, but may be applied generally to other areas of surgery where variable intensity illumination may be desired.

An embodiment of the variable-intensity endoilluminator of this invention can comprise an optical fiber, a stem (cannula) and a handpiece fabricated from biocompatible polymeric materials, such that the invasive portion of the illuminator can be a disposable surgical item. Embodiments of this invention fabricated from biocompatible polymeric materials can be integrated into a low cost, articulated handpiece mechanism, such that these embodiments can comprise an inexpensive disposable illuminator instrument.

Figure 1:
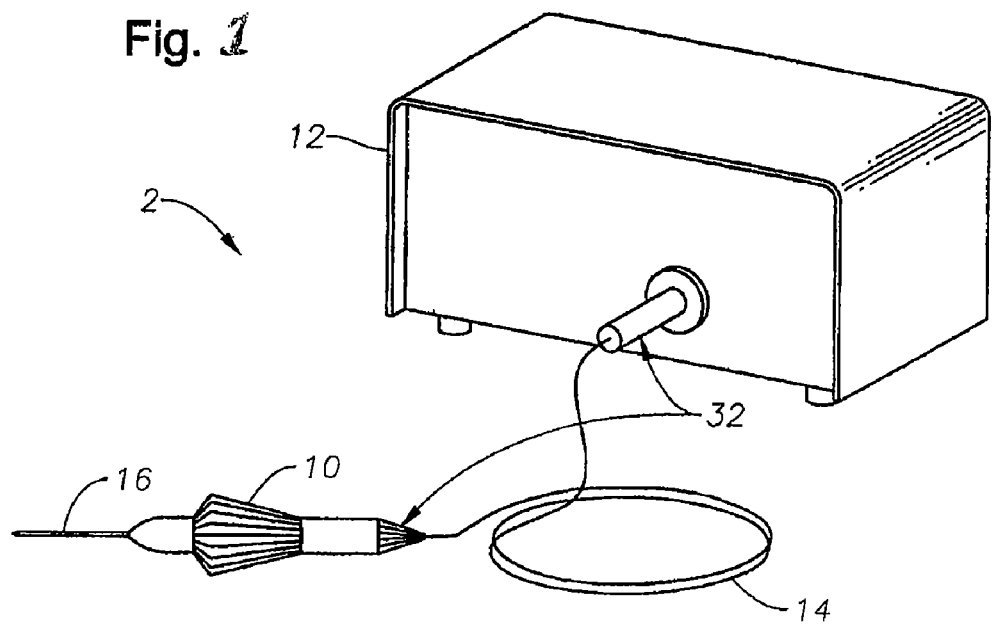
FIG. 1 is a diagrammatic representation of one embodiment of a system for variable intensity illumination in accordance with the teachings of this invention.

FIG. 1 is a diagrammatic representation of a surgical system 2 comprising a handpiece 10 for delivering a beam of relatively incoherent light from a light source 12 through cable 14 to a stem 16. Cable 14 can be any gauge fiber optic cable as known in the art, but is preferably a cable having 19, 20, 23 or 25 gauge fiber. Further, cable 14 can comprise a single optical fiber or a plurality of optical fibers optically coupled to receive and transmit light from light source 12 to stem 16 through handpiece 10. Stem 16 is configured to house an optical fiber 22, as is more clearly illustrated in FIG. 2. Coupling system 32 can comprise an optical fiber connector at each end of cable 14 to optically couple light source 12 to an optical fiber within handpiece 10, as discussed more fully below.

Figure 2:
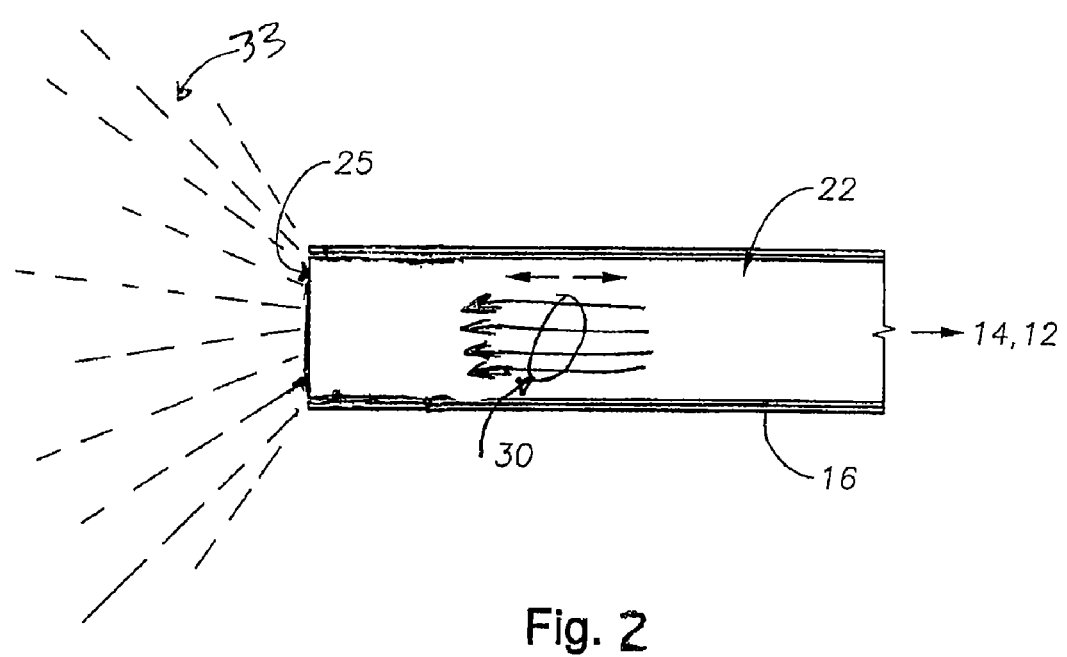
FIGS. 2 and 2A are more detailed diagrams of an embodiment of the present invention showing the stem and optical fiber in extended and retracted positions.

FIG. 2 is a magnified view of the distal end of stem 16 from FIG. 1. Stem 16 is shown housing optical fiber 22. Optical fiber 22 can be optically coupled to fiber optic cable 14. In some embodiments, fiber optic cable 14 can instead extend through the handpiece 10 and transmit light from light source 12 onto a surgical site directly, thus performing the function of optical fiber 22. For these embodiments, a separate optical fiber 22 is not used. When implemented within handpiece 10, optical fiber 22 is of a gauge compatible with the gauge of fiber optic cable 14, such that it can receive and transmit light from fiber optic cable 14. Handpiece 10 can be any surgical handpiece as known in the art, such as the Revolution-DSP™ handpiece sold by Alcon Laboratories, Inc. of Fort Worth, Tex. Light source 12 can be a xenon light source, a halogen light source, or any other light source capable of delivering relatively incoherent light to fiber optic cable 14. Stem 16 can be a small gauge cannula, preferably on the order of 19, 20, 23 or 25 gauge, as known to those having skill in the art. Stem 16 is preferably a suitable translucent biocompatible polymer (e.g., PEEK, polyimide, etc.), but can be manufactured of any suitable translucent material, as will be known to those having skill in the art, operable to diffuse and transmit light transmitted by optical fiber 22.

Figure 4:
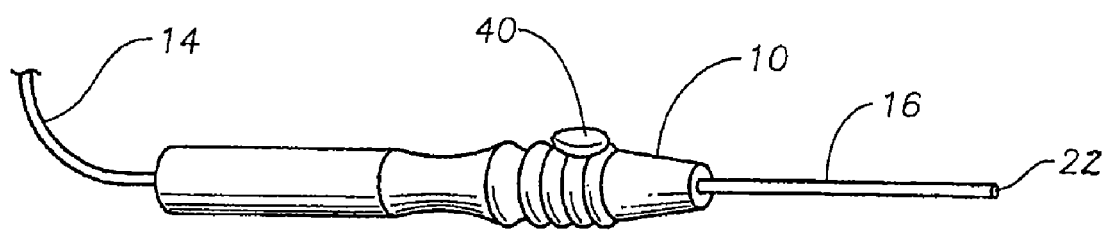
FIG. 4 is a diagram illustrating an embodiment of an adjusting means 40 in accordance with the present invention.

The optical fiber 22 (or fiber optic cable 14) housed within the stem 16 can be operably coupled to the handpiece 10, for example, via an adjusting means 40, as shown in FIG. 4. Adjusting means 40 can comprise, for example, a simple push/pull mechanism, such as a lever, or other mechanical, magnetic or electric displacement device as will be known to those having skill in the art for adjusting the linear displacement of the optical fiber 22. Light source 12 can be operably coupled to handpiece 10 (i.e., to optically couple light source 12 to optical cable 14/optical fiber 22) using, for example, standard SMA (Scale Manufacturers Association) optical fiber connectors at the end(s) of fiber optic cable 14. This allows for the efficient coupling of light from the light source 12 through fiber optic cable 14, through handpiece 10, and finally emanating from the distal end of optical fiber 22 either at the distal end of the stem 16, or diffused by stem 16 when optical fiber 22 is in a retracted position. Light source 12 may comprise filters, as known to those skilled in the art, to reduce the damaging thermal effects of absorbed infrared radiation originating at the light source. The light source 12 filter(s) can be used to selectively illuminate a surgical field with different colors of light, such as to excite a surgical dye.

Figure 2A:
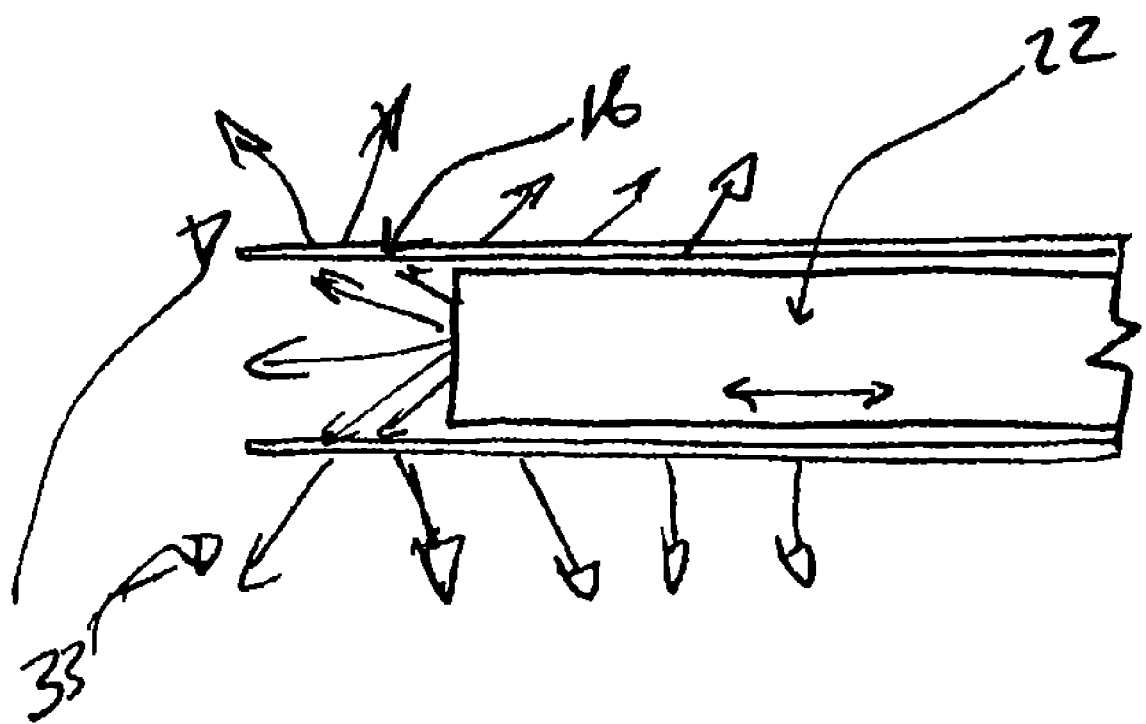

As shown in FIGS. 2 and 2A, optical fiber 22 is operable to transmit light in the manner of a conventional fiber optic probe to direct a spot beam at a desired location in the surgical field when optical fiber 22 is in a fully extended position, with the distal end 25 of optical fiber 22 coincident with the distal end of stem 16. Alternatively (FIG. 2A), optical fiber 22 can be retracted into stem 16 in a proximal direction such that the light emanating from the distal end of optical fiber 22 is incident on the inner surfaces of stem 16 and transmitted, in a diffused manner, through the translucent stem 16 to provide a more diffuse lighting of the surgical site. In this way, embodiments of the present invention are capable of providing more direct spot lighting or general peripheral lighting on demand, depending on the position of optical fiber 22 within stem 16. Optical fiber 22 can be retracted into stem 16 up to a desired stop point, such as co-incident with the scleral interface between the stem 16 and the sclera. Stem 16 can be a small-gauge cannula of about 19 to 30 gauge. Stem 16 is operably coupled to the handpiece 10, which can be either a re-usable or a disposable handpiece 10. Stem 16, in a preferred embodiment, is made of a flexible translucent material to provide flexibility in maneuvering the stem 16 to direct light from optical fiber 22 as may be desired by the surgeon, while remaining stiff enough to effectively use the endoilluminator.

Figure 3:
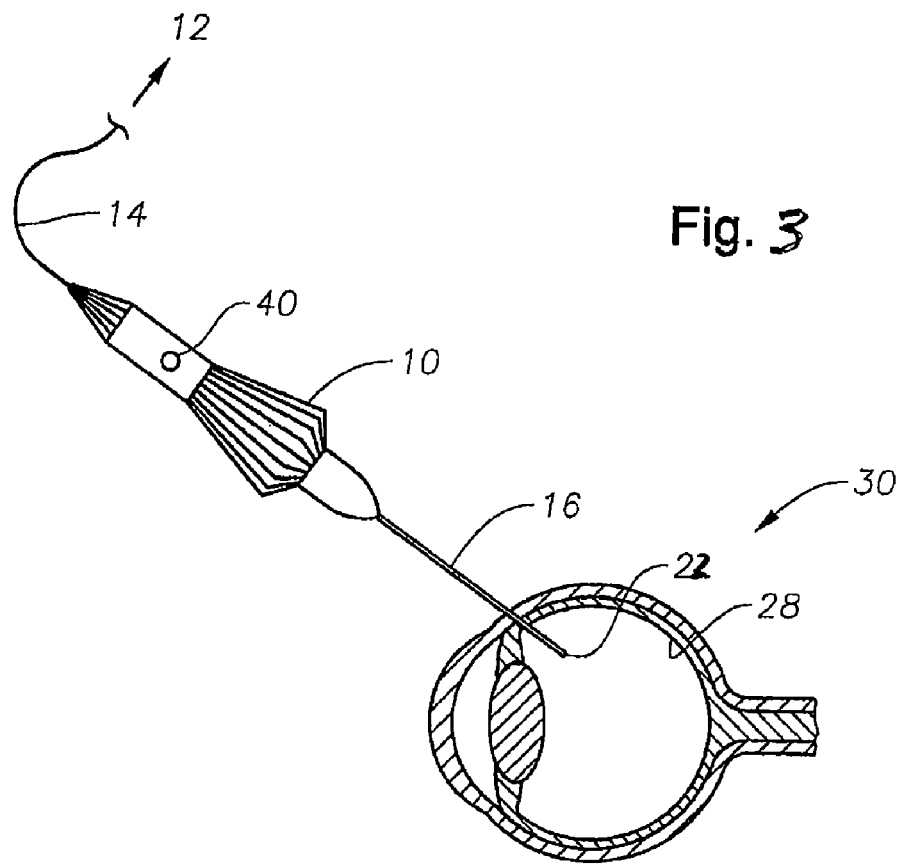
FIG. 3 is a diagram illustrating the use of an embodiment of a variable intensity illuminator of the present invention for ophthalmic surgery.

FIG. 3 illustrates the use of one embodiment of the variable intensity endoilluminator of this invention in an ophthalmic surgery. In operation, handpiece 10 delivers a beam of light through stem 16 via optical fiber 22 and/or fiber optic cable 14 to spot illuminate a retina 28 of an eye 30 (optical fiber 22 in an extended position). Alternatively, optical fiber 22 can be retracted to provide diffused light through stem 16 to generally illuminate the posterior chamber or desired peripheral areas. The collimated light delivered through handpiece 10 to optical fiber 22 is generated by light source 12 and delivered to illuminate the retina 28 by means of fiber optic cable 14 and coupling system 32. In this way, embodiments of the present invention can provide either a direct spotlight, such as a conventional fiber optic probe might, or a more diffused illumination via the translucent stem 16, as might a chandelier probe, but without undesirable shadows.

FIG. 5 provides another view of a variable intensity endoilluminator according to the teachings of this invention showing more clearly an embodiment of adjusting means 40. In this embodiment, adjusting means 40 comprises a slide button, as known to those skilled in the art. Activation of adjusting means 40 on handpiece 10 by, for example, a gentle and reversible sliding action, can cause the fiber 22/14 to laterally move within stem 16 by an amount determined and adjusted by sliding adjusting means 40. Adjusting the linear displacement of the optical fiber 22 within stem 16 in this way can be used to adjust the illumination provided by the embodiments of the present invention as discussed above.

Thus, the amount/type of illumination provided by optical fiber 22/stem 16 to illuminate the surgical field (e.g., the retina 28 of an eye 30) can be easily adjusted by a surgeon by adjusting the linear displacement of optical fiber 22. In this way, a surgeon can adjust the amount of light spread over a surgical field as desired to optimize the viewing field while minimizing glare. The adjusting means 40 of handpiece 10 can be any adjusting means known to those having skill in the art.

In one embodiment of the variable intensity endoilluminator of the present invention, a simple mechanical locking mechanism, as known to those skilled in the art, can permit the position of optical fiber 22 within stem 16 to be fixed, until released and/or re-adjusted by the user via the adjusting means 40.

An advantage of the embodiments of the variable intensity endoilluminator of this invention is that an operator can continuously vary the intensity and type of illumination provided by optical fiber 22/stem 16 to optimize viewing conditions within the surgical field. The pattern of light 33 from optical fiber 22 and/or stem 16 can thus be focused and controlled as desired by the operator. The embodiments of the illuminator of the present invention are therefore operable to adjust the intensity of the light provided by light source 12 to substantially cover the area of the surgical field desired by a surgeon.

Other embodiments of the variable intensity endoilluminator of this invention can comprise a stem 16 wherein at least a portion of stem 16 is opaque instead of translucent. In such an embodiment, the portion of stem 16 that does not transmit light can be positioned such that it prevents glare from obscuring the surgeon's view.

Although the present invention has been described in detail herein with reference to the illustrated embodiments, it should be understood that the description is by way of example only and is not to be construed in a limiting sense. It is to be further understood, therefore, that numerous changes in the details of the embodiments of this invention and additional embodiments of this invention will be apparent to, and may be made by, persons of ordinary skill in the art having reference to this description. It is contemplated that all such changes and additional embodiments are within the spirit and true scope of this invention as claimed below. Thus, while the present invention has been described in particular reference to the general area of ophthalmic surgery, the teachings contained herein apply equally wherever it is desirous to provide variable intensity illumination via a fiber optic probe.

What is claimed is:

1. A variable intensity illuminator, comprising:
   an optical fiber, optically coupled to a light source and operable to receive a light beam from the light source and transmit the light beam to illuminate a surgical field;
   a handpiece, operably coupled to the optical fiber;
   a translucent cannula, operably coupled to the handpiece, for housing and directing the optical fiber, wherein the cannula is operable to diffuse and transmit the light beam to provide general illumination of the surgical field when a distal end of the optical fiber is retracted into the cannula; and
   wherein the distal end of the optical fiber is operable to transmit the light beam to provide spot lighting of the surgical field when the distal end of the optical fiber is co-incident with a distal end of the cannula.

2. A variable intensity illumination surgical system comprising:
   a light source for providing a light beam;
   an optical cable, optically coupled to the light source for receiving and transmitting the light beam;
   a handpiece, operably coupled to the optical cable;
   an optical fiber, operably coupled to the handpiece, wherein the optical fiber is optically coupled to the optical cable to receive and transmit the light beam to illuminate a surgical field; and
   a translucent cannula, operably coupled to the handpiece, for housing and directing the optical fiber, wherein the cannula is operable to diffuse and transmit the light beam to provide general illumination of the surgical field when a distal end of the optical fiber is retracted into the cannula; and
   wherein the distal end of the optical fiber is operable to transmit the light beam to provide spot lighting of the surgical field when the distal end of the optical fiber is co-incident with a distal end of the cannula.

3. The illuminator or claim 1, wherein the surgical field is a selected portion of the interior of an eye.

4. The illuminator of claim 1, wherein the handpiece comprises an adjusting mechanism coupled to the optical fiber to control the linear displacement of the optical fiber within the cannula.

5. The illuminator of claim 4, wherein the adjusting mechanism comprises a locking mechanism to hold the optical fiber at a selected position relative to the cannula.

6. The illuminator of claim 1, wherein the cannula is made of a flexible translucent material.

7. The illuminator of claim 1, wherein the cannula is translucent along only a portion of its length.

8. The illuminator of claim 1, wherein the cannula is a 20 gauge cannula.

9. The illuminator of claim 1, wherein the cannula is a 23 gauge cannula.

10. The illuminator of claim 1, wherein the cannula is a 25 gauge cannula.

* * * * *